(12) United States Patent
Ishida et al.

(10) Patent No.: US 6,577,039 B2
(45) Date of Patent: Jun. 10, 2003

(54) DRIVING SYSTEM AND ACTUATOR

(75) Inventors: Yuichi Ishida, Kanagawa (JP); Naomi Nagasawa, Kanagawa (JP); Masayuki Suzuki, Kanagawa (JP); Takaaki Ami, Kanagawa (JP); Teiichiro Nishimura, Kanagawa (JP)

(73) Assignee: Sony Corporation, Tokyo (JP)

( * ) Notice: Subject to any disclaimer, the term of this patent is extended or adjusted under 35 U.S.C. 154(b) by 344 days.

(21) Appl. No.: 09/739,224

(22) Filed: Dec. 18, 2000

(65) Prior Publication Data

US 2001/0029401 A1 Oct. 11, 2001

(30) Foreign Application Priority Data

Dec. 16, 1999 (JP) .............................................. 11-357807

(51) Int. Cl.$^7$ .............................. A61F 2/08; B01D 15/00
(52) U.S. Cl. ................................ 310/300; 91/6; 623/26
(58) Field of Search ................................ 310/300; 91/6; 359/241; 204/157.15; 252/582; 623/26

(56) References Cited

U.S. PATENT DOCUMENTS

| 5,021,064 A | * | 6/1991 | Caines ......................... 623/26 |
| 5,436,372 A | * | 7/1995 | Yoshida et al. .............. 564/291 |
| 5,992,825 A | * | 11/1999 | Vollenweider, II ........ 254/93 R |
| 6,400,489 B1 | * | 6/2002 | Suzuki et al. ................ 359/241 |

* cited by examiner

Primary Examiner—Thomas M. Dougherty
(74) Attorney, Agent, or Firm—Sonnenschein, Nath & Rosenthal

(57) ABSTRACT

A driving system using an intercalation substance as a novel mechanochemical system includes an actuator using the intercalation substance and driven by exchange of solutions or by changing concentration of a solution, and a solution supplier that supplies the actuator with the driving solution or solutions. The actuator is composed of one or more cylindrical or fiber-shaped elements each extending in the expanding and contracting direction of the intercalation substance, or one or more film-shaped or plate-shaped elements each having a major surface extending vertically of the expanding and contracting direction of the intercalation substance. The driving system is used as artificial muscle, for example.

43 Claims, 12 Drawing Sheets

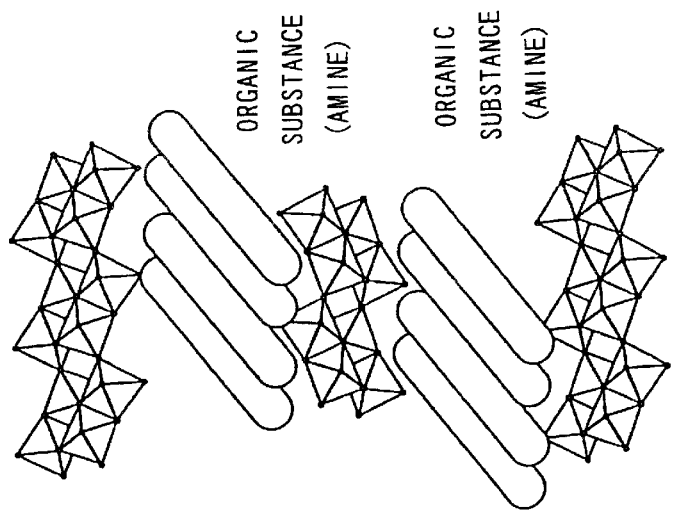
*Fig. 1A* KTiNbO$_5$  c=1.82nm
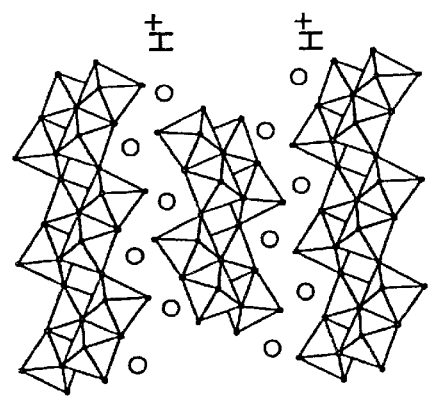
*Fig. 1B* HTiNbO$_5$  c=1.75nm
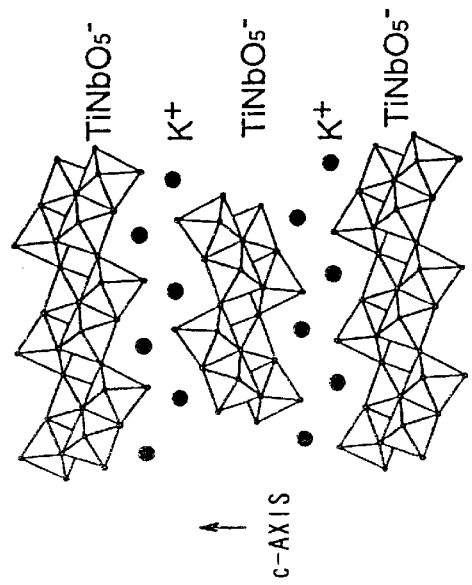
*Fig. 1C* RNH$_2$·HTiNbO$_5$  c≥2nm

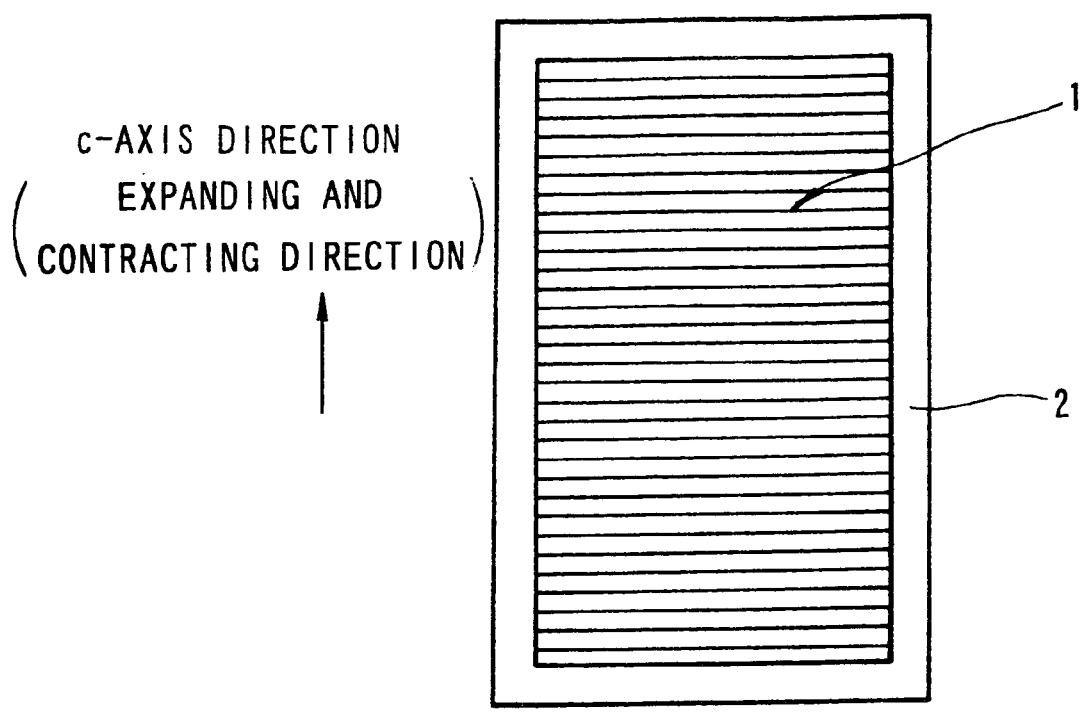

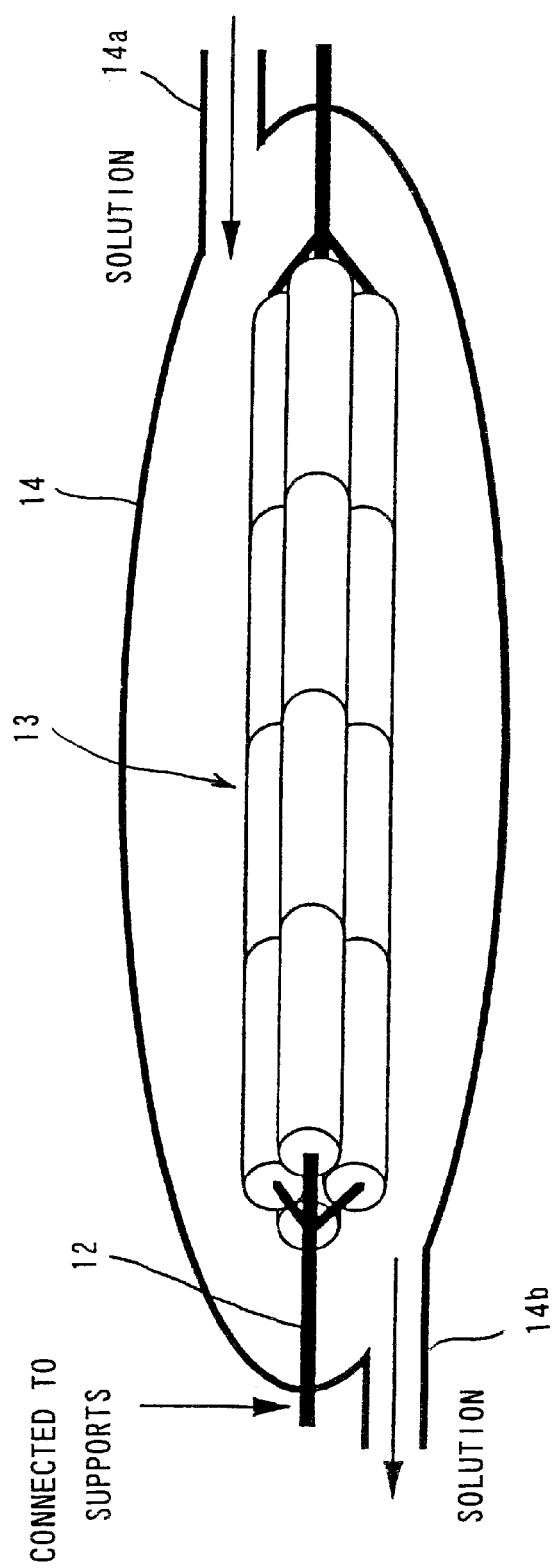

DRIVING SYSTEM AND ACTUATOR

RELATED APPLICATION DATA

The present application claims priority to Japanese Application No. P11-357807 filed Dec. 16, 1999, which application is incorporated herein by reference to the extent permitted by law.

BACKGROUND OF THE INVENTION

1. Field of the Invention

This invention relates to a driving system and actuator using an intercalation substance. More particularly, the invention relates to a driving system configured to convert a chemical energy supplied by using an intercalation substance directly into a mechanical energy and externally work with a driving force derived from the mechanical energy, which is suitable for application to technical fields of artificial intelligence robots, microelectronics, medical services, and so forth.

2. Description of the Related Art

Most of currently available actuators are electrically driven actuators, such as like electromagnetic motors and electrostrictive devices (piezoelectric devices), and those driven by fluid pressures, such as hydraulic actuators and pneumatic actuators. As far as they are used in various kinds of automated factory machinery and various kinds of transport machinery, existing actuators exhibit practically sufficient performances.

However, for use in autonomous robots under the need for emergent development, for example, actuators are required to operate with three-dimensional freedom of motion in cooperation with each other. In such cases, a force exerted by an actuator and its weight becomes a load to another actuator, and therefore, as the freedom increases, difficulty in controllability and total weight increase enormously. In these applications, muscle in living bodies can be said to be well-balanced actuators. In numerical values, displacement of living muscle is 50% in the direction of contraction, response time is 30 ms, developed tension is $(2\sim10)\times10^4$ $kgf/m^2$ ($2\sim10$ $kgf/cm^2$), and maximum generated output is per unit weight is $(0.1\sim0.3)\times10^3$ W/kg ($0.1\sim0.3$ W/g). No actuators satisfying these all have been developed yet (Applied Physics Vol. 60, No. 3 (1991), p. 258).

Polymeric gel is being remarked as artificial muscle similar to living muscle. Although some kinds of polymeric gel drives upon application of an electric field, generally employed are mechanochemical systems (or chemomechanical systems) that repeats swelling and contraction depending upon environmental changes such as temperature, pH, solution concentration, and so on, while converting chemical reaction energies directly to mechanical energies. Mechanochemical systems, themselves, employ living muscle as well, there are no examples in artificial substances other than organic polymeric materials such as polymeric gels, rubbers and collagen, for example (T. Takamori, "Actuator Revolution", Kogyo-chosakai, 1987). Mechanochemical systems have a lot of advantages, such as being light, soft, and noiseless, and generating no exhaust gas by combustion. However, since most of currently developed polymeric materials are in amorphous states, and their structures have no anisotropy, they are interior in dynamic strength and durability.

On the other hand, most of inorganic layered materials represented by clay mineral are called intercalation materials, and can incorporate ions and molecules between layers by application of an electric field or chemical interaction. At that time, they change in lattice constant and volume. Therefore, these materials may become the third mechanochemical systems next to living muscle and polymeric materials.

As far as the Inventor is aware, as actuators using intercalation materials, there are currently those disclosed in:

Japanese Patent Laid-Open No. hei 02-131376
Japanese Patent Laid-Open No. hei 04-127885
Japanese Patent Laid-Open No. hei 05-110153
Japanese Patent Laid-Open No. hei 06-125120

Summarizing these actuators, the actuator disclosed in Japanese Patent Laid-Open No. hei 02-131376 has a structure sandwiching an electrolytic polyethylene oxide by graphite inter-layer compound such that flexion occurs by transpiration of Li between layers. The actuator disclosed in Japanese Patent Laid-Open No. hei 4-127885 is one of a series using $Ag_{0.7}V_2O_5$ as its positive/negative poles and using $4AgI$-$Ag_2WO_4$ as its solid electrolyte. These actuators are such that ions are intercalated by application of an electric field and a change in volume is used as a driving force. Actuators disclosed in Japanese Patent Laid-Open No. hei 05-110153 and Japanese Patent Laid-Open No. hei 06-125120 are such that an electric field is applied from the exterior to a compound prepared by inserting a polar organic substance such as amine to an organic layered substance such as clay mineral, and displacement is obtained by changing the orientation angle of the organic substance existing between inorganic layers.

As reviewed above, all of conventional actuators using intercalation substances employ a driving system by application of an electric field and no reports have heretofore taught direct conversion of chemical energies to mechanical energies.

On the other hand, according to the knowledge of the Inventor, it can be expected that advanced actuators used in artificial intelligence robots or autonomous robots requiring drive portions having great freedom can obtain excellent properties that living muscle has.

However, as already discussed above, because it is only polymeric materials that conventional systems can be artificially made of, most of them are amorphous and their structures have no anisotropy, they have drawbacks in mechanical strength and durability.

OBJECT AND SUMMARY OF THE INVENTION

It is therefore an object of the invention to provide a driving system using an actuator that uses an intercalation substance and becomes a new mechanochemical system removing those drawbacks.

Toward solution of the above-mentioned problems involved in the conventional techniques, the Inventor made researches and reviews that are summarized below.

As discussed above, all actuators using conventional intercalation substances were of types driven by application of electric fields. Through various reviews, the Inventor has come to the conclusion that the most suitable advanced actuator would be an actuator of a mechanochemical system using an intercalation substance and driven by converting chemical energies supplied by a solution directly into mechanical energies. This actuator is driven by a chemical technique, more particularly, by ingress and egress of a guest substance in and from a space between layers of an inorganic layered substance as a host substance due to chemical interaction by a supply of a solution from the exterior. This actuator can be configured as a muscle-shaped actuator (artificial muscle) creating giant displacement by using a single-crystal or c-axis-oriented film as the intercalation substance and stacking it in the c-axis direction that is the direction of expansion and contraction. Especially by using inorganic molecules having a large molecular length, giant displacement can be obtained more effectively.

The present invention has been made based the above-outlined reviews.

Toward a solution of the above-discussed problems, according to the invention, there is provided a driving system comprising:

an actuator using an intercalation substance and driven by exchange of solutions or by changing concentration of a solution; and solution supply means for supplying the actuator with driving solution.

In the present invention, although the actuator is typically immersed in the solution supplied from the solution supply means, its entirety is not always in contact with the solution, but only a part thereof may be in contact with the solution. The solution contains a guest substance as explained later.

The actuator may comprise either a single element (module or unit) or a combination of a plurality of elements to obtain a desired size.

Basically, the actuator may have any shape, and it is designed in accordance with the purpose of its use. More specifically, the actuator may be in form of a cylinder or a prism having its axis in expansion and contraction direction of the intercalation substance, or a fiber. Preferably, for the purpose of its shape upon changes in distance between layers caused by intercalation reaction, the actuator is coated with an elastic, porous inorganic polymer that defines fine holes permitting the solution to pass through, at least on a part of the side surface, or typically on the entire surface. The coating, however, may be omitted. The actuator typically has a structure in which a plurality of cylindrical, prismatic or fiber-shaped elements are serially connected, or a structure in which a plurality of the said structures each serially connecting a plurality of cylindrical, prismatic or fiber-shaped elements are connected in parallel(or bound together). For the purpose of not preventing expanding and contracting actions, individual elements are integrally coupled by bonding or other means.

The actuator may have a form of a film or plate in which the expanding and contracting direction of the intercalation substance is vertical to the major surface. Preferably, for the purpose of maintaining its shape upon changes in layer-to-layer distance caused by intercalation reaction, the actuator is coated with an elastic, porous inorganic polymer that defines fine holes permitting the solution to pass through, at least on a part of the side surface, or typically on the entire surface. The coating, however, may be omitted. The actuator typically has a structure in which a plurality of film-shaped or plate-shaped elements are serially connected, or a structure in which a plurality of the said structures each serially connecting a plurality of film-shaped or plate-shaped elements are connected in parallel (or bound together). For the purpose of not preventing expanding and contracting actions, individual elements are integrally coupled by bonding or other means.

The actuator may be made of an element made by shaping powdered intercalation substance into a predetermined shape. Preferably, for the purpose of its shape upon changes in distance between layers caused by intercalation reaction, the actuator is coated with an elastic, porous inorganic polymer that defines fine holes permitting the solution to pass through, at least on a part of the side surface, or typically on the entire surface. The coating, however, may be omitted. The actuator is typically mad up of a structure in which a plurality of elements each made by shaping a powdered intercalation substance are connected in series, or made up of a structure in which a plurality of the said structures each made up of the serially connected elements each made by shaping the powdered intercalation substance are connected in parallel (or bound together). For the purpose of not preventing expanding and contracting actions, individual elements are integrally coupled by bonding or other means.

Alternatively, the actuator may be made by bonding an intercalation substance around a tubular hollow member of an elastic material defining fine holes permitting the solution to pass through such that the expanding and contracting direction of the intercalation substance is parallel to the axial direction of the hollow member. In this case, the solution is supplied into interior of the hollow member from the solution supply means. Subject to the purpose of its use, a hollow yarn, for example, may be used as the hollow member.

The actuator may be made by appropriately combining various types of elements mentioned above, depending upon the purpose of its use.

The actuator may have a bimorph structure in which a first actuator using a first intercalation substance and a second actuator using a second intercalation substance are bonded vertically to the expanding and contracting direction of the first intercalation substance and the second intercalation substance, or a unimorph structure in which an intercalation substance the an elastic member are bonded vertically to the expanding and contracting direction of the intercalation substance. In the former case, the first and second intercalation substances may be either identical or different. Between the first actuator and the second actuator, an elastic member (such as organic polymeric material like a fluorine-series resin or a metal like Pt), for example, may be interposed. These may be used also as the elastic member in the latter case.

The solution supply means is preferably configured to supply the solution to the actuator while recovering and reusing the solution. In other words, it is configured to circulate the solution. Alternatively, the solution supply means may be configured to supply the solution to the actuator while replacing at least a part of the solution by a corresponding amount of fresh solution.

Typically, the actuator is contained in a container, and the solution supply means includes at least one solution supply tube connected to one or the other end of the container to define a closed path passing through the container. Normally, a plurality of the solution supply tubes are provided such that different solutions can be supplied. Preferably, a drainage treatment portion (drainage refiner) is provided enroute of these solution supply tubes to refine solution discharged from the container and from a pump for sending solution to the container. The drainage treatment portion refines solution by ion exchange, for example.

In a typical example, the solution supply tube includes a first solution supply tube for supplying a first solution which expands the intercalation substance and a second solution supply tube for supplying a second solution that contracts the intercalation substance. In this case, to enable switching of the solutions to be supplied to the container, the first solution supply tube and the second solution supply tube are normally connected to one and the other ends of the container via control valves controlled in opening and closing motions in response to expansion and contraction of the actuator.

The actuator may be used in combination with one or more such actuators, depending upon the way of its use. For example, a first actuator and a second actuator may be used as the actuator such that these first and second actuators share a common support and antagonistically expand or contract.

In the present invention, the actuator is basically applicable to any purposes provided they use expanding and contracting movements. However, from the viewpoint of flexibility and litheness of movements, application to artificial muscle is suitable. Especially, when the first actuator and the second actuator share a common support for antagonistic movements, the actuator provides movements similar to those of living muscle.

In the present invention, the host substance of the intercalation substance is typically a substance containing at least one kind of inorganic layered substance whereas the guest substance of the intercalation substance is ions or molecules such that ingress and egress of the guest substance in and from a space between layers of the inorganic layered substance as the host substance change the layer-to-layer distance and there by drives the actuator. The host substance may be an inorganic/organic composite substance that comprises an inorganic layered substance as its matrix, and at least one kind of organic substance intercalated between layers of the inorganic layered substance such that the host substance is changed in distance between its layers by ingress and egress of a guest substance and thereby drives the actuator. Typically, the host substance immersed in a solution containing the guest substance, and by replacement of the solution containing the guest substance with a solution not containing the guest substance, or by changes in concentration of the solution containing the guest substance, reversible egress and ingress of the guest substance relative to a space between layers of the host substance change the distance of the space between the layers and thereby activate the actuator. The guest substance is typically an organic substance, and particularly an organic material having at least one polar functional group in at least one of its carbon positions. Substances having this feature are ammonium, amine, aniline, amino acid, uric acid, alcohol, hydrazine, aldehyde, acetone, acrylonitrile, sugar, pyridine, phosphine, ethylene oxide, and so on.

The inorganic layered substance as the host substance may be, for example, at least one kind of substance selected from the group consisting of layered perovskite, niobium-series substances, layered perovskite copper-series substances, layered titanium niobates, layered halite oxides, transition metal oxides bronze-series substances, transition metal oxochlorides, layered polysilicates, layered clay minerals, hydrotalcites, transition metal chalcogenides, phosphoric acid zirconates and graphite. Specific examples of these substances are shown below.

(1) layered perovskite niobium-series substances:
    $KLaNb_2O_7$, $Kca_2Nb_3O_{10}$, $RbCa_2Nb_3O_{10}$, $CsCa_2Nb_3O_{10}$, $KNaCa_2Nb_4O_{13}$
(2) layered perovskite copper-series substances:
    $Bi_2Sr_2CaCU_2O_8$, $Bi_2Sr_2Ca_2Cu_3O_{10}$
(3) layered titanium niobates $KTiNbO_5$, $K_2Ti_4O_9$ or $K_4Nb_6O_{17}$
(4) layered halite oxides:
    $LiCoO_2$, $LiNiO_2$
(5) transition metal oxide bronze-series substances:
    $MoO_3$, $V_2O_5$, $WO_3$, $ReO_3$
(6) transition metal oxochlorides:
    FeOCl, VOCl or CrOCl
(7) layered polysilicates:
    $Na_2O\text{-}4SiO_2\text{-}7H_2O$
(8) layered clay minerals:
    smectite, vermiculite, mica
(9) hydrotalcites:
    $Mg_6Al_2(OH)_{16}CO_3\text{—}H_2O$
(10) transition metal chalcogenides:
    $TaSe_2$, $TaS_2$, $MOS_2$, $Vse_2$
(11) phosphoric acid zirconates:
    $Zr(HPO_4)_2nH_2O$
(12) graphite:
    C In the present invention, an acidic solution and/or alkali metal hydroxide solution are typically used for disconnecting the guest substance from the host substance. Usable as the acidic solution are hydrochloric acid, nitric acid, fluoric acid, sulfuric acid, and soon. Usable as the alkali metal hydroxide solution are KOH and others. Especially when the guest substance is amine, the use of hydrochloric acid is effective for disconnecting the guest substance from the host substance.

According to the driving system proposed by the invention having the above summarized structure, since it uses the actuator using an intercalation substance and driven by switching solutions or changes in concentration of a solution, it is possible to obtain a driving system of a mechanochemical system that converts chemical energy directly to mechanical energy to use it as a driving force.

The above and other objects and features of the present invention will become apparent from the following detailed description and the appended claims with reference to the accompanying drawings.

BRIEF DESCRIPTION OF THE DRAWINGS

FIGS. 1A, 1B and 1C are schematic diagrams that show crystallographic structures of $KTiNbO_5$, $HTiNbO_5$ and $RNH_2$—$HTiNbO_5$;

FIG. 5 is a cross-sectional view that shows an actuator using an intercalation substance;

FIG. 7 is a schematic diagram that shows a driving system according to the first embodiment of the invention;

DETAILED DESCRIPTION OF THE PREFERRED EMBODIMENTS

Explained below are embodiments of the invention with reference to the drawings.

Before starting explanation of driving systems according to embodiments of the invention, explanation is made about a specific example of intercalation substances that can be used for actuators of the driving systems.

FIGS. 1A through 1C show crystallographic structures of $KTiNbO_5$-series intercalation compounds. $KTiNbO_5$ as a matrix substance has a layered structure sandwiching K ions ($K^+$) between oxide layers of Ti—Nb—O, and the c-axis length of its unit lattice is c=1.82 nm (FIG. 1A). $K^+$ between oxide layers may be replaced with other ions, such as H ions ($H^+$), and in this case, c=1.75 nm (FIG. 1B). It is also possible to incorporate organic molecules such as amine between the oxide layers, an in this case, there occurs changes as large as c≧2 nm in response to changes in distance between the layers (FIG. 1C).

Linear-chain alkylamine was experimentally intercalated into $KTiNbO_5$ ceramics up to 16 in number of carbon atoms. Its fabrication procedures are briefly explained below.

Commercially available source materials $K_2CO_3$, $TiO_2$ and $Nb_2O_5$ in powder were collected by the mol ratio of K:Ti:Nb=1:1:1, and sufficiently mixed. Thereafter, the mixture was calcined for 24 hours at 900° C. and then crushed. Steps of mixing, calcination and crushing were repeated three times, and a single-phase powder sample of $KTiNbO_5$ was obtained.

After that, the sample underwent ion exchange treatment 60° C. for one hour in 2N hydrochloric acid, and $HTiNbO_5$ in powder was prepared.

The next and later steps are intercalation of linear-chain alkylamine. Since there is a difference in solvent and other factors, depending upon the number of carbon atoms, respective cases are explained respectively.

(1) In case of carbon atoms being 1 through 5:

Pure water was used as the solvent. In its amine solution of 1 mol/l, $HTiNbO_5$ in the rate of 0.05 mol/l was mixed, and the solution was stirred at the room temperature for two hours and thereafter left for three days for drying.

(2) In case of carbon atoms being 8 or 10:

Mixed liquid containing pure water and ethanol by 50:50 (in volume ratio) was used as the solvent. In its amine solution of 1 mol/l, $HTiNbO_5$ in the rate of 0.05 mol/l was mixed, and the solution was stirred at the room temperature for two hours and thereafter left for three days for drying.

(3) In case of carbon atoms being 12 or 16:

Mixed liquid containing pure water and ethanol by 50:50 (in volume ratio) was used as the solvent. In its amine solution of 1 mol/l, $HTiNbO_5$ in the rate of 0.05 mol/l was mixed, and the solution was stirred at the room temperature for two hours and immediately centrifuged for 10 minutes to promote precipitation. Then, after discarding its supernatant fluid, it was left for two days for drying.

Figure 2:
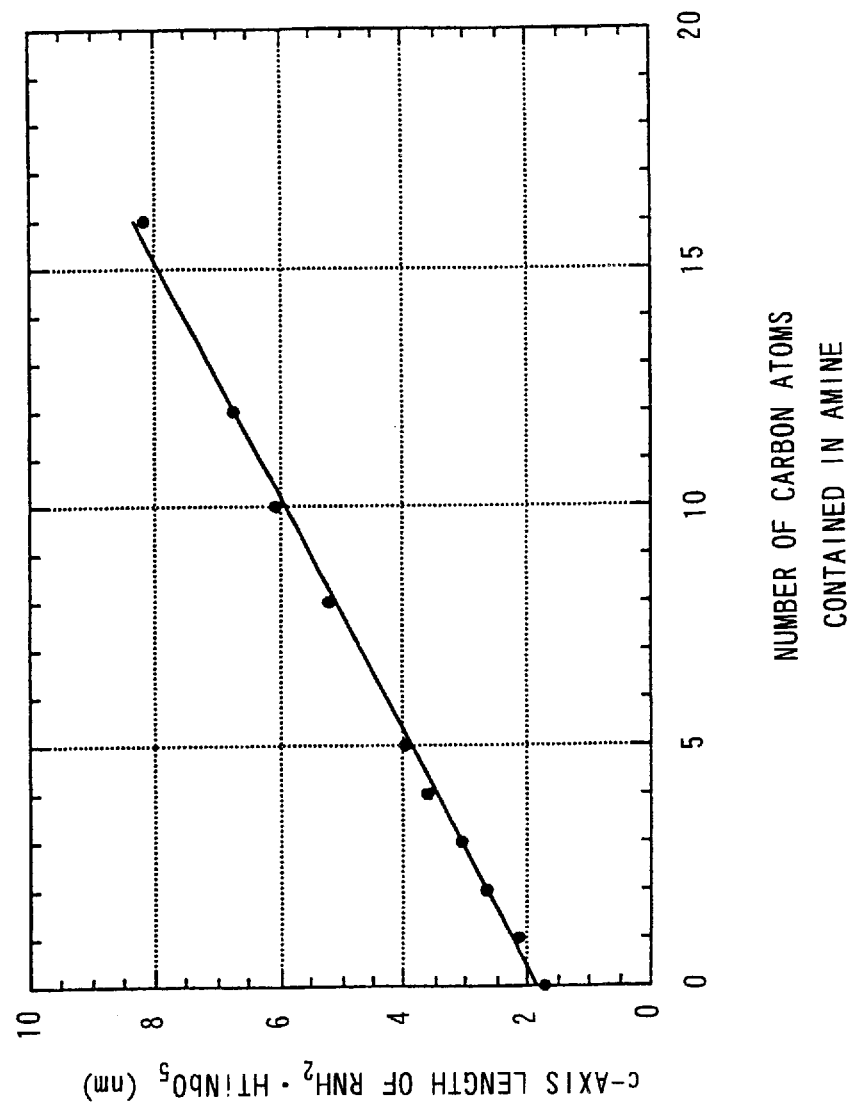
FIG. 2 is a schematic diagram that shows a relation between the number of carbon atoms contained in linear-chain alkylamine ($RNH_2$) and -axis constant of $RNH_2$—$HTiNbO_5$.

FIG. 2 shows changes in c-axis length with increase of carbon atoms in the above-explained experiment. As shown in FIG. 2, in the case where amine with 16 carbon atoms was introduced, c-axis length of 8.2 nm was approximate 4.8 times the x-axis direction of 1.7 nm of $HTiNbO_5$, and the unit lattice large expanded in the x-axis direction. At that time, there were almost no changes in a-axis length and b-axis length. The relational expression between the c-axis lattice constant $C_0$ and the number of carbon atoms n can be approximated in the clear linear form as $$C_0=1.847+0.40741n$$

In this manner, when linear-chain alkylamine is used, as the number of carbon atoms contained therein is large (that is, molecular length is large), displacement obtained by intercalation reaction becomes large.

As explained above, inter-layer compound using $KTiNbO_5$ as its matrix substance exhibits a large expansion of the x-axis length when amine is introduced. In order to efficiently extract this expansion as a macro phenomenon, it is ideal to use single crystal $KTiNbO_5$. So, a method for processing the single crystal is next explained, and changes x-axis lattice constant in individual steps are shown. It is shown here that intercalation reaction of amine, in particular, has a reversibility, and it is therefore a practical mechanochemical system.

Figure 3:
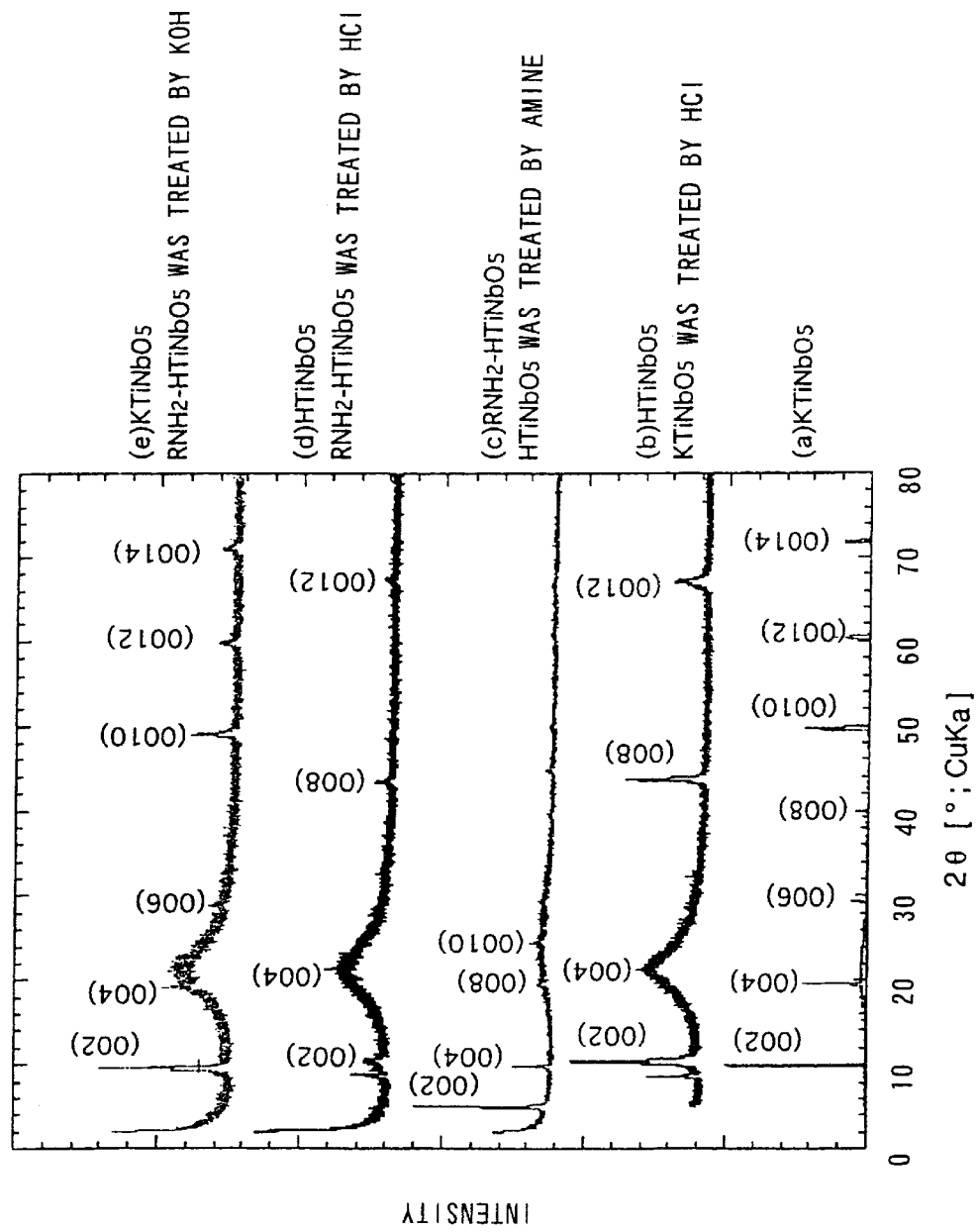
FIG. 3 is a schematic diagram that shows an X-ray diffraction pattern of amine-$KTiNbO_5$-series intercalation compound single crystal.

Fabrication of $KTiNbO_5$ Single Crystal $KTiNbO_5$ powder was introduced into a platinum crucible, and the platinum crucible was maintained in the atmospheric air at 1400° C. for five hours and thereafter cooled to 1150° C. gradually by the cooling rate of 10° C./h. For sintering, a double-crucible method was employed. Namely, the formed mass was entered in a platinum crucible of 20 ml, and this platinum crucible was entered in a larger aluminum crucible and hermetically closed with an aluminum cover. Then the molten, solidified mass, thus obtained, was removed from the platinum crucible, and a clear, transparent single-crystal piece was selected. $KTiNbO_5$ crystal is typically plate-shaped, reflecting the anisotropy of he crystallographic structure, and single crystal as large as approximately $(2~3)\times10^{-3}m\times(2~3)\times10^{-3}m\times(1~2)\times10^{-3}m$, in maximum, can be obtained by extracting it by a mechanical process. An X-ray diffraction pattern of the obtained $KTiNbO_5$ crystal is shown at (a) in FIG. 3. From (a) of FIG. 3, the diffraction peak of (001) is solely observed, and the measured surface of the sample is confirmed to be a c-plane. The c-axis lattice constant calculated from the (002) peak in that pattern was 1.80 nm. Broad diffraction derives from glass of the substrate holder. As a result of quantitative analysis of the composition by EDX, the metal composition ratio was K:Ti:Nb=0.97:1.0:0.98.

Fabrication of $HTiNbO_5$ Single-crystal ($KTiNbO_5 \rightarrow HTiNbO_5$)

The above $KTiNbO_5$ crystal was entered in 1N HC1 and left to stand for two weeks. In this process, K ions in the $KTiNbO_5$ crystal are replaced by H ions, and $HTiNbO_5$ crystal was obtained. There is no substantial change in shape of the crystal from $KTiNbO_5$ before the ion exchange. An X-ray diffraction pattern of the obtained $HTiNbO_5$ crystal is shown at (b) in FIG. 3. The c-axis lattice constant calculated from the (002) diffraction in that pattern was 1.70 nm, and slightly smaller than that of $KTiNbO_5$. A result of quantitative analysis of the composition by EDX was K:Ti:Nb= 0.97:1.0:0.98, and disconnection of almost all K components was confirmed.

Intercalation of Organic Substance ($KTiNbO_5 \rightarrow C_4H_9NH_2$—$HTiNbO_5$)

With the $HTiNbO_5$ single crystal thin piece thus obtained, n-butylamine ($C_4H_9NH_2$) was intercalated. Pure water was used as the solvent, and amine solution of 1 mol/1 was prepared. Then, under the condition with a far excessive mol ratio of amine relative to $HTiNbO_5$, they were left for interaction at the room temperature for three days. In this process, single crystal of intercalation compound ($C_4H_9NH_2$—$HTiNbO_5$) with n-butylamine intercalated between layers of $HTiNbO_5$ was obtained. An X-ray diffraction pattern of the obtained $C_4H_9NH_2$—$HTiNbO_5$ single-crystal is shown at (c) in FIG. 3. The c-axis lattice constant calculated from the (002) diffraction in that pattern was 3.55 nm, and expansion of 2.1 times was confirmed as compared with that of $HTiNbO_5$.

Reversibility 1 in Intercalation of Organic Substance ($C_4H_9NH_2$—$HTiNbO_5 \rightarrow HTiNbO_5$)

With the $C_4H_9NH_2$—$HTiNbO_5$ single-crystal thin piece thus obtained, treatment by hydrochloric acid was again conducted. Immersing this single-crystal thin piece into 2N hydrochloric acid, and left for interaction at the room temperature for seven days. An X-ray diffraction pattern of the single-crystal after treatment by hydrochloric acid is shown at (d) in FIG. 3. The c-axis lattice constant calculated from the (002) diffraction in that pattern was 1.68 nm, and the single-crystal was confirmed to have returned to $HTiNbO_5$. Thus the intercalation of n-butylamine has a reversibility, and using this principle, repetitive driving is possible by changing solutions. That is, the intercalation compound expands when immersed in amine solution, and contracts when immersed in hydrochloric acid solution.

Reversibility 2 in Intercalation of Organic Substance ($C_4H_9NH_2$—$HTiNbO_5 \rightarrow HTiNbO_5$)

After that, with the $C_4H_9NH_2$—$HTiNbO_5$ single-crystal thin piece, treatment by KOH solution was conducted. Immersing this single-crystal thin piece into KOH solution of 2 mol/1, and left for interaction at the room temperature for six days. An X-ray diffraction pattern of the obtained sample is shown at (e) in FIG. 3. The c-axis lattice constant calculated from the (002) diffraction in that pattern was 1.88 nm, and close to that of $KTiNbO_5$. Further, since the result of quantitative analysis by EDX was K:Ti:Nb=0.97:1:0.98, the substance was confirmed to have substantially returned to $KTiNbO_5$.

Figure 4:
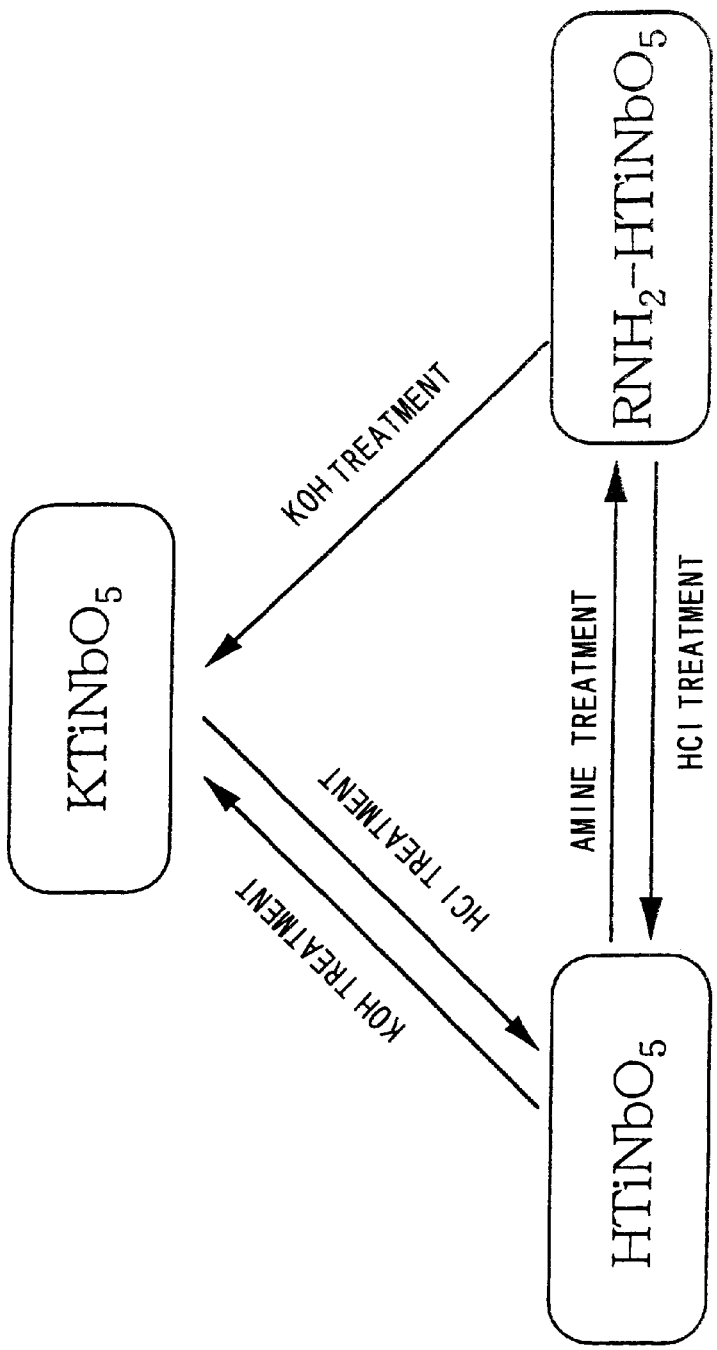
FIG. 4 is a schematic diagram that shows reversibility of amine-$KTiNbO_5$-series intercalation substance.

Reversible properties of the above-explained amine-$KTiNbO_5$-series intercalation substances can be summarized as shown in FIG. 4. From FIG. 4, amine-intercalated crystal can be returned to $HTiNbO_5$ by using hydrochloric acid, and can be returned to $KTiNbO_5$ by using KOH solution. Regarding reversibility of ion exchange between $KTiNbO_5$ and $HTiNbO_5$, there is a report by Kikkawa et al (S. Kikkawa, M. Koizumi, Physica, 105B (1981) 234–237). Regarding reversibility between amine-$HTiNbO_5$ and $HTiNbO_5$, there is a report by Grandin et al (A. Grandin, M. N. Borel, B. Raveru: J. Solid State Chemistry, 60 (1985) 366–375). As to reversibility between amine-$HTiNbO_5$ and $KTiNbO_5$, the Inventor is aware of no report heretofore, and it should be a novel matter that was first found by the Inventor.

n-butylamine was intercalated into the $HTiNbO_5$ single-crystal obtained in the above-explained process, and its displacement was directly detected. Its results is explained below. For measurement of displacement, anon-contact laser displacement meter was used. $HTiNbO_5$ single-crystal having the thickness of $0.20 \times 10^{-3}$ was immersed into butylamine solution of 1 mol/1, and left undisturbed for two hours. After drying, thickness of the single-crystal was measured and confirmed to be $0.61 \times 10^{-3}$ m, which shows expansion by approximately three times. Although this is a slightly larger value as compared with expansion of the c-axis length to approximately 2.1 times as measured in the above-explained example, this is mainly caused by voids between layers, which are produced during intercalation. In this manner, intercalation substance provides sufficiently large displacement for practical use as an actuator, and it could be measured actually.

When actually fabricating an actuator using an intercalation substance, it is necessary to stack single-crystals or oriented films of the intercalation substance in the expanding and contracting direction, i.e. the c-axis direction.

Large displacement can be obtained also by using films oriented in the c-axis direction in lieu of intercalation to single-crystals explained above. As to a way of making oriented films, it can be made by adding $HTiNbO_5$ powder into amine solution and casting the suspension. According to Lambert et al, using amine with the number of carbon atoms up to 3, oriented films can be readily obtained in that process (J. -F. Lambert, Z. Dend, J. -B. D'espinose and J. J. Fripiat, J. Colloid and Interface Science, 132 (1989) 337–351).

FIG. 5 shows an actuator that is used in a driving system according to the first embodiment of the invention. As shown in FIG. 5, the actuator is made of a cylindrical intercalation substance 1 having a center axis coinciding with the c-axis direction and coated on the circumferential surface and opposite end surfaces, that is, on the entire surface, with porous organic polymer 2. Although the intercalation substance 1 used here is cylindrical, what is important is that the x-axis direction of the intercalation substance 1 coincides with the expanding and contracting direction of the actuator, and the shape may be rectangular, or any other shape. Since in and out movements of ions or molecules occur in parallel with layers in intercalation substances, for the purpose of increasing the response speed, it is necessary to decrease the diameter of the cylindrical intercalation substance 1. However, if the diameter of the intercalation substance 1 is decreased excessively, separation and crumbling of layers are liable to occur. Therefore, for the purpose of maintaining the shape, the porous organic polymer 2 is coated on the surface of the intercalation substance 1. The porous organic polymer 2 has fine holes that hold a host substance and permits a guest substance to pass through, and also has an elasticity not applying a load during expansion or contraction of the intercalation substance 1. Usable as the porous organic polymer 2 is, for example, fluorine-contained rubber, which is excellent in resistivity to chemicals.

Figure 6A:
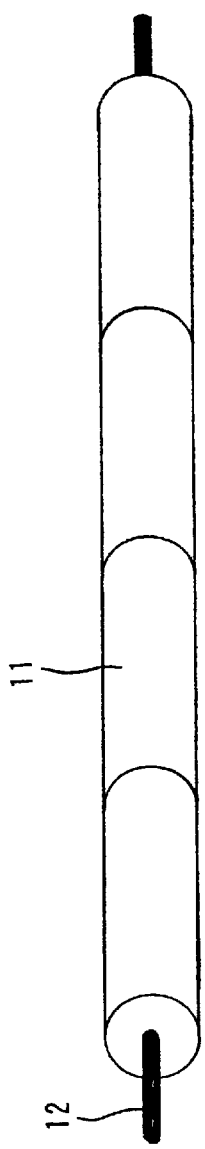
FIGS. 6A and 6B are perspective and cross-sectional views that show a fiber-shaped actuator.
Figure 6B:
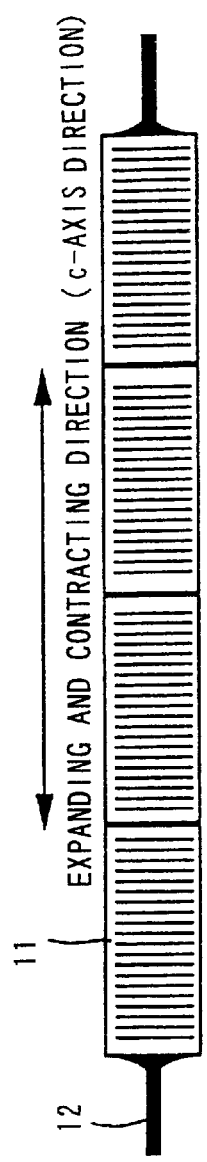

FIGS. 6A and 6B show a fiber-shaped actuator including a plurality of serially, coaxially connected actuators 11 as shown in FIG. 5. The actuators 11 at opposite ends have transmission rods 12 for externally transmitting its driving force. Although the actuator is shown in FIG. 6 as having four actuators 11 connected, this is only an example, and the number of actuators 11 may be determined as desired. For connecting these actuators 11 to each other, an adhesive suitable for the series (epoxy-series adhesive, for example, when using fluorine-contained rubber as the porous organic polymer 2) may be used, or the porous organic polymer 2 coated on opposite end surfaces of the intercalation substance 1 may be used as an adhesive.

The first embodiment uses an actuator binding a plurality of fiber-shaped actuators shown in FIGS. 6A and 6B into a shape similar to living muscle. That is, as shown in FIG. 7, in the driving system according to the first embodiment, the actuator 13 is made by binding a plurality of fiber-shaped actuators (four actuators, shown here) shown in FIGS. 6A and 6B while simultaneously binding transmission rods at opposite ends of the respective fiber-shaped actuators. The actuator 13 is contained in a container 14, and transmission rods 12 at its opposite ends are led out outside the container 14 and connected to external supports (not shown) to which its driving force should be transmitted. One and the other ends of the container 14 have a solution inlet 14a and a solution outlet 14b, respectively, such that a driving solution supplied from a solution supply source (not shown) is introduced into the container 14 from the inlet 14a while the solution is discharged from the container 14 through the solution outlet 14b. Solution is changed in response to expansion and contraction of the actuator 13. More specifically, if an amine-$KTiNbO_5$-series intercalation substance, mentioned above, is used, amine is supplied for expanding the actuator 13 and hydrochloric acid is supplied for contracting the actuator 13.

As explained above, according to the first embodiment, since the actuator 13 uses an intercalation substance and is driven by changing solutions, it is possible to obtain a diving system using the actuator of a mechanochemical system driven by chemical reaction alone without the need for application of an electric field. This driving system is suitable for application to artificial muscle similar to living muscle.

Figure 8:
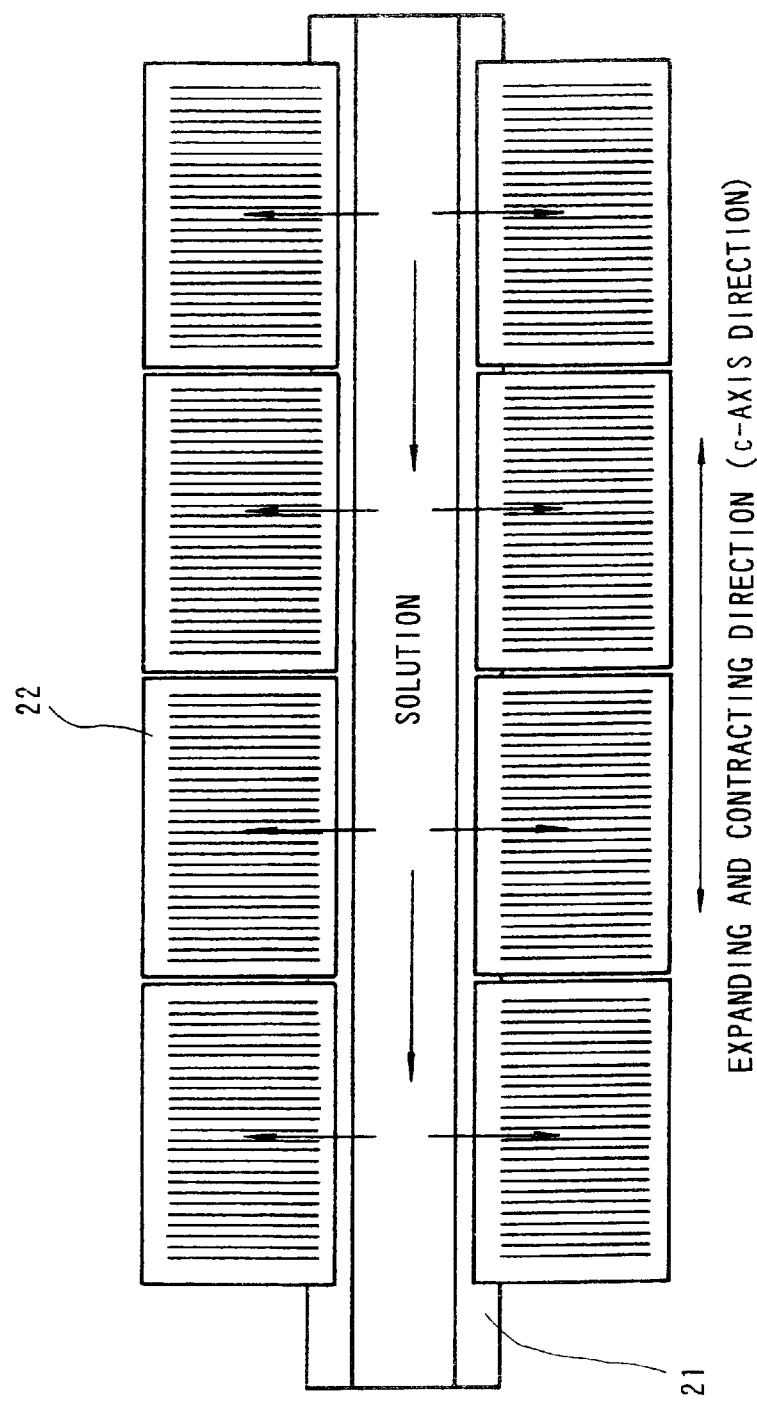
FIG. 8 is a schematic diagram that shows a driving system according to the second embodiment of the invention.

FIG. 8 shows a driving system according to the second embodiment of the invention.

To efficiently utilize a solution for driving an actuator, its supply requires a contrivance. That is, as miniaturization of actuators progresses, paths for supplying a solution become miniaturized, and selection of materials suitable for the paths is important. In the second embodiment, hollow yarns are remarked as a material of paths, and combinations of hollow yarns and intercalation substances have been devised. That is, as shown in FIG. 8, in the driving system according to the second embodiment, the actuator is made by bonding an intercalation substance 22 outside a hollow yarn 21 to surround it. The x-axis direction of the intercalation substance 22 coincides with the center axis of the hollow yarn 21. A driving solution from a solution supply source (not shown) can flow through the hollow yarn 21. The hollow yarn 21 expands and contracts together with the intercalation substance 22, and a solution flows into the intercalation substance 22 from the bonded portion between the hollow yarn 21 and the intercalation substance 22. Usable as materials of the hollow yarn 21 are polyvinyl alcohol-series materials and polyacrylonitrile-series materials, for example.

According to the second embodiment, In addition to the same advantages as those of the first embodiment, the following advantages can be obtained. That is, in the driving system according to the first embodiment in which the actuator is made by binding fiber-shaped actuators, as the bundle becomes thicker, the solution becomes more difficult to reach the central portion of the bundle. In contrast, in the second embodiment, since the intercalation substance 22 is bonded outside the hollow yarn 21 and a solution supplied inside the hollow yarn 21 flows into the intercalation substance 22 through the bended portion, the solution can be sufficiently supplied to deep portions of the actuator even when its diameter is large. Then, since the solution quickly spread to the entirety of the intercalation substance 22 forming the actuator, its response speed is improved. Additionally, combination with the hollow yarn 21 improves the strength and other structural reliability.

Figure 9:
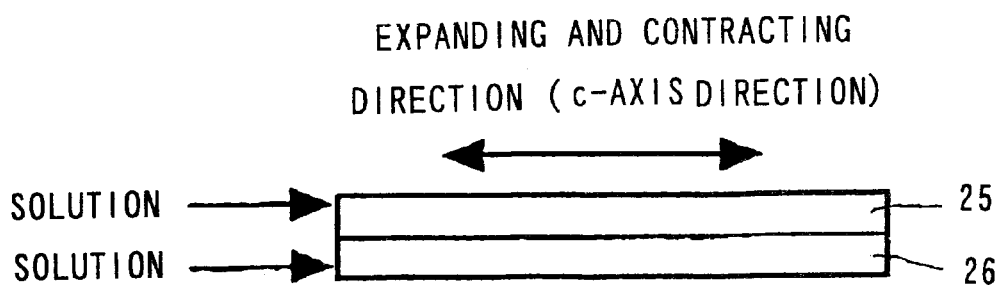
FIG. 9 is a schematic diagram that shows a driving system according to the third embodiment of the invention.

FIG. 9 shows a driving system according to the third embodiment of the invention.

As shown in FIG. 9, the driving system has a bimorph structure in which two film-shaped or plate-shaped actuators 25 and 26 made of the same intercalation substance or different intercalation substances are bonded vertically of the c-axis direction, i.e. expanding and contracting direction of the intercalation substance or substances. Each of these actuators 25 and 26 is made up of a plurality of hollow yarns (not shown) extending in parallel with each other and in parallel with the expanding and contracting direction along a common plane in equal intervals, for example, and entirely buried in a film-shaped or plate-shaped intercalation substance. A driving solution from a solution supply source (not shown) is supplied inside the hollow yarns. Each hollow yarn expands and contracts together with the intercalation substance, and a solution flows into the intercalation substance from the bonded portion between the hollow yarn and the intercalation substance. Usable as materials of the hollow yarn are polyvinyl alcohol-series materials and polyacrylonitrile-series materials, for example. The actuators 25 and 26 are completely sealed from each other by an adhesive, for example, at their bonded portion to prevent solutions supplied to hollow yarns of the actuators 25 and 26 from mixing with each other.

Figure 10:
FIG. 10 is a schematic diagram for explaining behaviors of the driving system according to the third embodiment of the invention.

A method for driving the driving system is explained below. Assume here that amine-$KTiNbO_5$-series intercalation substances are used as intercalation substances forming the actuators. For example, by supplying hydrochloric acid to one of the actuators 25 and 26 through its hollow yarns while supplying amine solution to the other from its hollow yarns, or by changing concentration of solutions supplied to the actuators 25 and 26, a large flexion can be generated. FIG. 10 shows an aspect of flexion that occurs when hydrochloric acid is supplied to the actuator 25 while amine solution is supplied to the actuator 26, for example.

According to the third embodiment, in addition to the same advantages as those of the first embodiment, it is possible to obtain the additional advantage that displacement caused by an increase of the layer-to-layer distance of the intercalation substances due to the above-mentioned flexion.

Figure 11:
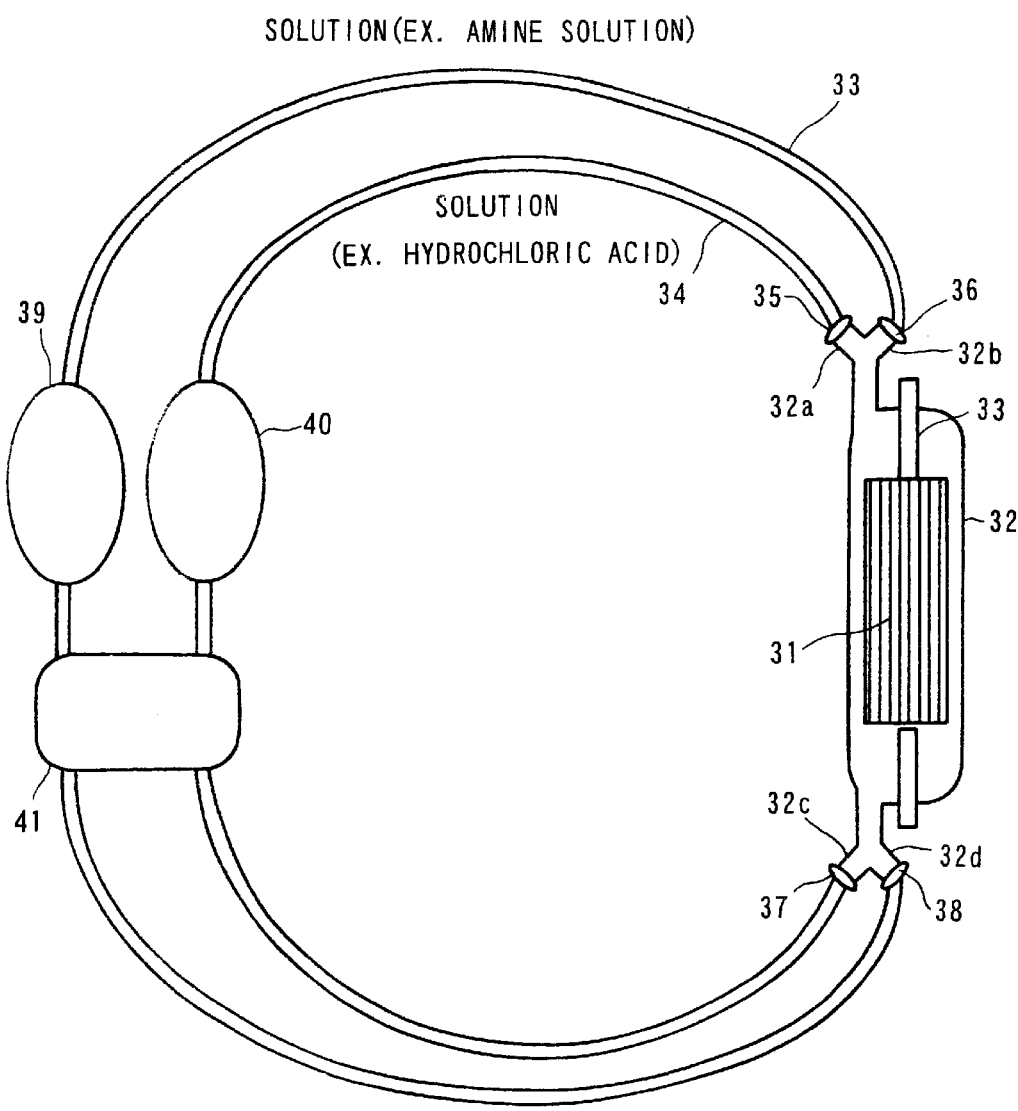
FIG. 11 is a schematic diagram that shows a driving system according to the fourth embodiment of the invention.

FIG. 11 shows a driving system according to the fourth embodiment of the invention. This driving system is an artificial muscle driving system.

As shown in FIG. 11, the driving system comprises artificial muscle 31 and a solution supply system for driving the artificial muscle 31. Usable as the artificial muscle 31 are actuators according to the first embodiment or second embodiment, for example. The artificial muscle 31 is contained in a container 32, and transmission rods 33 at opposite ends of the artificial muscle 31 are led out outside the container 32. At one end of the container 32, bifurcated solution inlets 32a and 32b are provided. At the other end, again bifurcated solution outlets 32c and 32d are provided. Between the solution inlet 32a and the solution outlet 32c and between the solution inlet 32b and the solution outlet 32d, solution supply tubes 33 and 34 are connected, respectively. Supply of the solution to the container 32 and discharge of the solution from the container 32 are controlled by valves 35, 36, 37, 38 provided at the solution inlets 32a, 32b and the solution outlets 32c and 32d, respectively. Pumps 39 and 40 are provided enroute of the solution supply tubes 33, 34 to send out solutions. Further, a drainage treatment portion 41 is provided enroute of the solution supply tubes 33, 34 for the purpose of refining solutions and using them again because it is impossible to prevent that the solutions used for driving the artificial muscle 31 mix with each other.

As an example of solutions for driving the artificial muscle 31, when the above-mentioned amine-$KTiNbO_5$- series intercalation substances are used, amine solution is supplied to the solution supply tube 33 as the solution for expanding the artificial muscle 31, and hydrochloric acid is supplied to the solution supply tube 34 as the solution for contracting the artificial muscle 31. More specifically, In this case, the solution supply tube 33 is filled with amine solution of 1 mol/l whereas the solution supply tube 34 is filled with hydrochloric acid of 1N, and pressures larger than 1 atmospheric pressure are always applied to the inner wall of the solution supply tubes 33, 34 by the pumps 39, 40. Then, by opening or closing the valves 35, 36, 37 and 38, these amine solution and hydrochloric acid are supplied alternately to the artificial muscle 31.

Refinement of solutions in the drainage treatment portion 41 is conducted by using an ion exchange film, for example, in a concrete example. That is, solutions used in the artificial muscle 31 and discharged from the container 32 are filtered through an ion exchange film and refined in the drainage treatment portion 41, and again supplied to the pumps 39, 40. Usable as the ion exchange film is an element made by introducing ion exchange radicals as polar radicals into perfluorine-contained polymers or a styrene-series copolymer as its base material. More specifically, a Nafion film, for example, can be used. In the case where a cation exchange film having sulfone radicals ($-SO_3^-$) as its polar radicals, by supplying solutions through this film, amine components become alkylammonium ions and are trapped by the sulfone radicals. Therefore, drainage passing through the cation exchange film becomes hydrochloric acid solution and can be used again. In this case, since amine components are consumed in the cation exchange film, an additional amount of amine components has to be supplied. On the other hand, in the case where an anion exchange film having quaternary ammonium radicals ($-NR_3^+$) (R is a methyl radical $-CH_3$, for example) as its polar radicals is used, chlorine ions are removed, and the amine solution can be used again. In this case, hydrochloric acid has to be supplied additionally.

Figure 12:
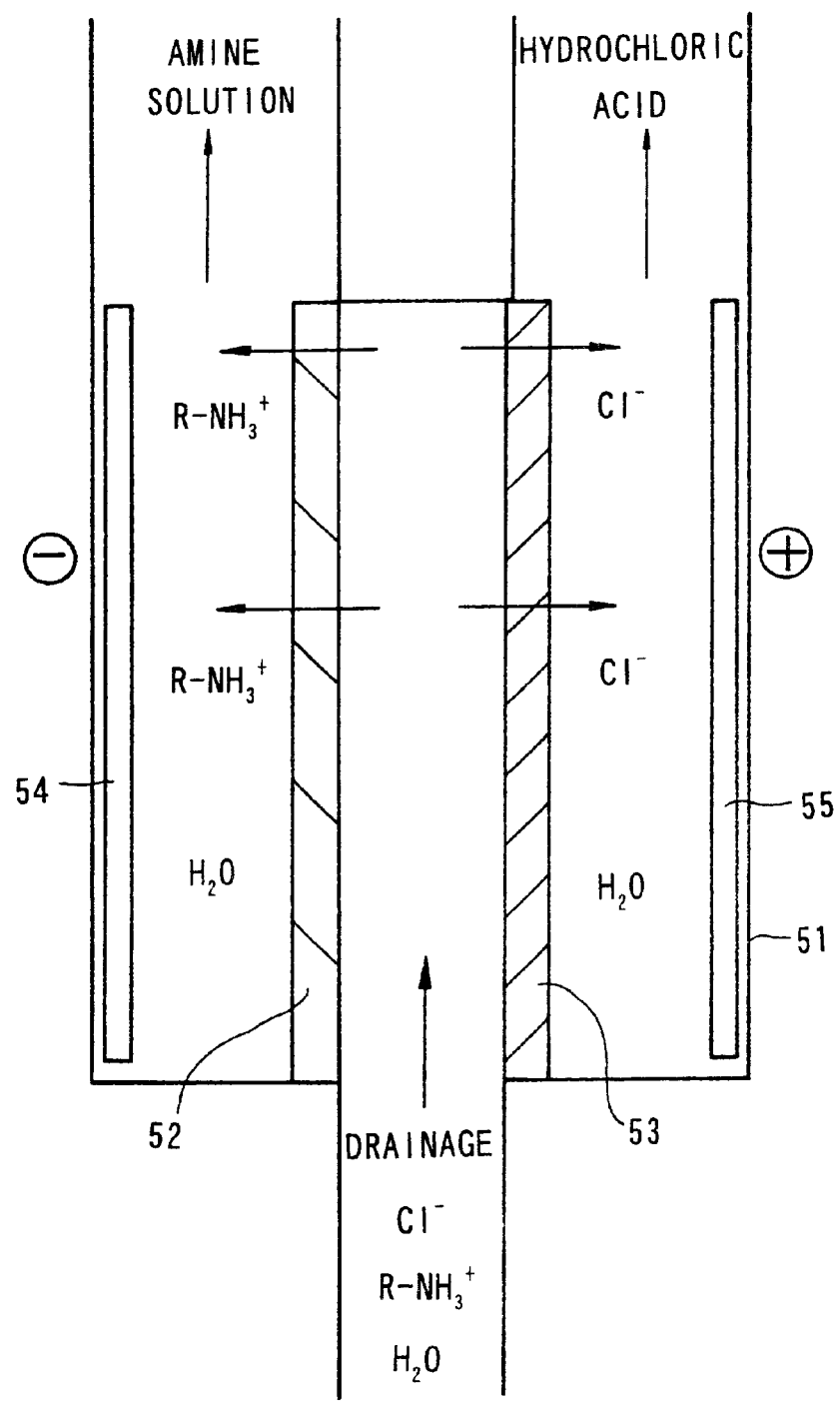
FIG. 12 is a schematic diagram for explaining a specific example of a drainage treatment portion in the driving system according to the fourth embodiment of the invention.

As a refined system not requiring additional supply of amine or hydrochloric acid, FIG. 12 shows an example of the drainage treatment portion 41 using both a cation exchange film and an anion exchange film. As shown in FIG. 12, in a drainage path 51 extending from an inlet for introducing a solution containing amine and hydrochloric acid in mixture to bifurcated outlets, at positions where the path is bifurcated, a cation exchange film 52 and an anion exchange film 53 are provided, respectively, and electrodes 54 and 55 are provided on the inner wall of the drainage path 51 in confrontation with the cation exchange film 52 and the anion exchange film 53. When a minus voltage is applied to the electrode 54 on the part of the cation exchange film 52 and a plus voltage is applied to the electrode 55 on the part of the anion exchange film 53, cations (alkylammonium ions) in the solution pass through the cation exchange film 52, and anions (chlorine ions) pass through the anion exchange film 53. As a result, alkylammonium ion solution, i.e., amine solution, is obtained as a refined product at the negative pole, i.e., electrode 54, and hydrochloric acid is obtained as another refined product at the positive pole, i.e., electrode 55.

According to the fourth embodiment, in addition to the same advantages as those of the first embodiment, it has the additional advantage that solutions necessary for driving the artificial muscle 31 can be recycled, and therefore, it is possible to realize an artificial muscle driving system saving resources and careful to the environment.

Figure 13:
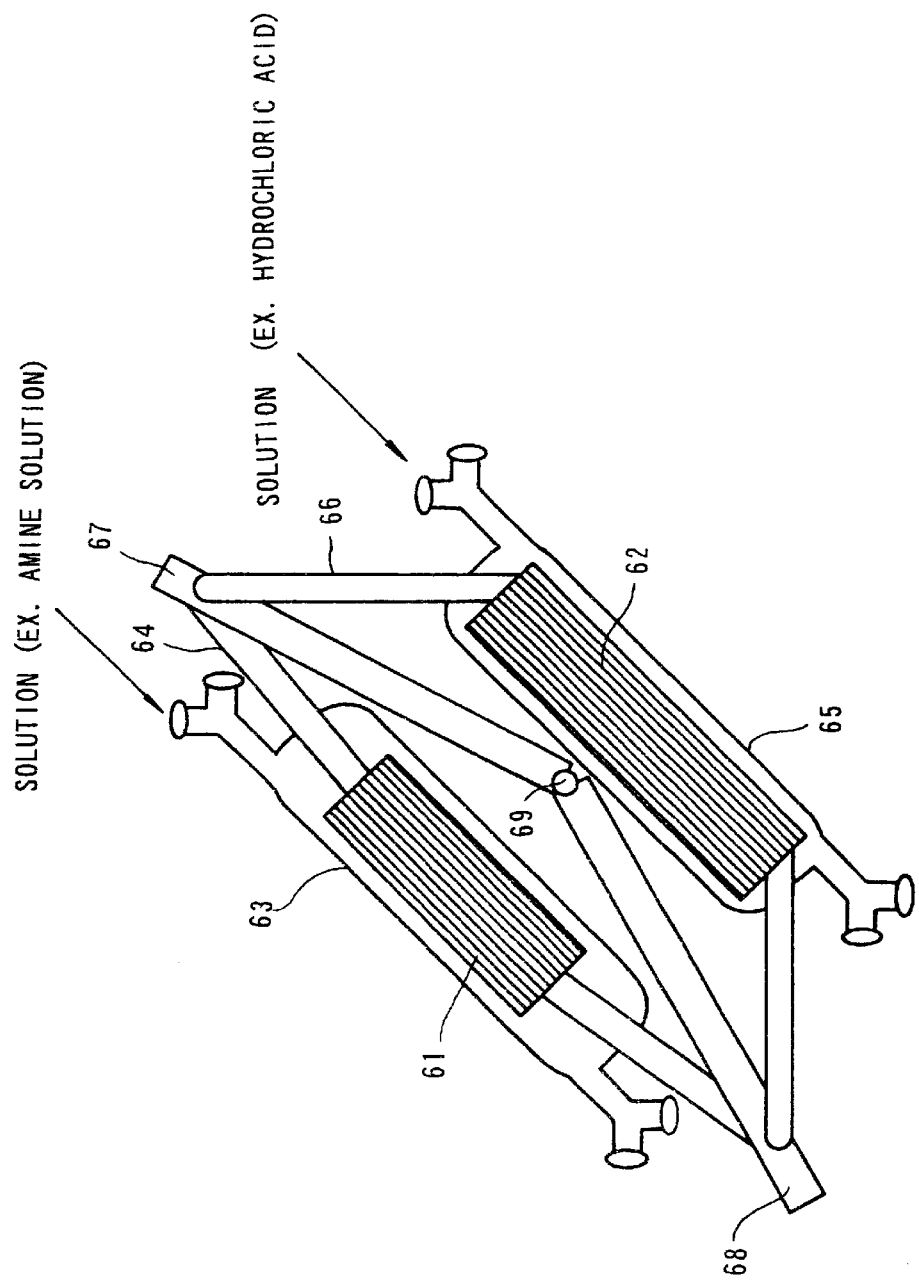
FIG. 13 is a schematic diagram that shows a driving system according to the fifth embodiment of the invention.

FIG. 13 shows a driving system according to the fifth embodiment of the invention. This driving system is an artificial antagonistic muscle driving system.

As shown in FIG. 13, this driving system combines two artificial muscles 61, 62. Usable as these artificial muscles 61 and 62 are actuators according to the first embodiment or the second embodiment, for example. The artificial muscle 61 is contained in a container 63, and transmission rods 64 at opposite ends of the artificial muscle 61 are led out outside the container 63. Similarly, the artificial muscle 62 is contained in a container 65, and transmission rods 66 at opposite ends of the artificial muscle 62 are led out outside the container 65. The transmission rods 64 and 66 at common ends of the artificial muscles 61 and 62 are connected to a support 67. Similarly, the transmission rods 64 and 66 at the other common ends of the artificial muscles 61 and 62 are connected to a support 68. These supports are coupled together through a joint 69, and can rotate about the joint 69.

Although not shown, at opposite ends of the containers 63, 65, solution inlets and solution outlets are provided and connected to solution supply tubes, and solution send-out pumps, drainage treatment portions, and so on, are attached to these solution supply tubes. However, these features as the same as those of the fourth embodiment, and are omitted from explanation.

In the fifth embodiment, the artificial muscles 61, 62 perform antagonistic operations with respect to supports 67, 68 which correspond to living bones. That is, cooperative movements of the artificial muscles 61, 62 provide motions similar to that of antagonistic muscles. For example, in the state shown in FIG. 13, while the artificial muscle 61 contracts, the artificial muscle 62 expands to the contrary. In an examples of solutions used for driving these artificial muscles 61, 62, if amine-$KTiNbO_5$-series intercalation substances explained above, amine solution is supplied to one of the artificial muscles 61, 62 to be expanded, and hydrochloric acid is supplied to the other to be contracted.

According to the fifth embodiment, in addition to the same advantages as those of the first embodiment, it is possible to obtain the additional advantage that well-balanced movements can be provided than the mode of independently driving each artificial muscle because two artificial muscles 61, 62 are combined to form antagonistic muscles.

Having described specific preferred embodiments of the present invention with reference to the accompanying drawings, it is to be understood that the inventions is not limited to those precise embodiments, and that various changes and modifications may be effected therein by one skilled in the art without departing from the scope or the spirit of the invention as defined in the appended claims.

For example, numerical values, structures, materials, processes, and so on, suggested in the foregoing embodiments are not but mere examples, and any other appropriate numerical values, structures, materials, processes, etc. can be used if so desired.

As described above, according to the invention, since the driving system comprises an actuator using an intercalation substance and driven by exchange of solutions or changes in concentration of a solution, and a solution supply means for supplying an actuator driving solution, the following effects are obtained.

That is, since the actuator is a mechanochemical system capable of changing a chemical energy directly into a mechanical energy, it has the following general advantages.

(1) It uses a chemical interaction as the driving force, and does not need complicated peripheral devices such electrodes and wirings.

(2) It is driven noiselessly, without generating exhaust gas by combustion, or other undesired products.

(3) Since the actuator is used while immersed in a liquid, lithe motor functions can be obtained.

By he use of an intercalation substance to form the actuator, the following advantages are obtained.

(1) By using an inorganic skeleton as a host substance, excellent durability is obtained.

(2) By using an organic substance having a large molecular length as a guest substance, giant displacement can be produced.

(3) Inorganic and organic combination is possible in the molecular level, and it is possible to realize a composite material having both a strength of the inorganic substance and a flexibility of the organic substance, and obtain a high-performance actuator.

(4) By utilizing a high anisotropy, higher response speed and higher energy converting efficiency can be expected.

As reviewed above, intercalation substances can be mechanochemical materials that exceed all conventional polymeric materials. Especially in comparison with polymeric gels, by using an intercalation substance including an inorganic substance as its skeleton, excellent strength and durability are obtained, and since it has a layered structure, by using its anisotropy, response speed and energy converting efficiency can be improved. In this manner, it is possible to realize an actuator of a composite material similar to living muscle having both a strength of an inorganic substance and a flexibility of an organic substance.

Although an actuator itself can be driven with a chemical energy, an electric system will be required for sending control signals at least to valves and pumps. Nevertheless, the driving system according to the invention needs much less consumption power than conventional driving systems that also use electromagnetic motors as actuators. Thus, the invention can realize an artificial muscle system less in power consumption, flexible, and noiselessly driven, and thereby contributes to progressing developments of self-controlled robots, for example.

What is claimed is:

1. A driving system comprising:
   an actuator using an intercalation substance and driven by exchange of solutions or by changing concentration of a solution; and
   solution supply means for supplying said actuator with driving solution.

2. The driving system according to claim 1 wherein said actuator is immersed in the solution supplied from said solution supply means.

3. The driving system according to claim 1 wherein said actuator is at least partly in contact with the solution supplied from said solution supply means.

4. The driving system according to claim 1 wherein said actuator is made up of a single element or a combination of a plurality of elements.

5. The driving system according to claim 1 wherein said actuator has a cylindrical or fiber-shaped configuration extending in the expanding and contracting direction of said intercalation substance.

6. The driving system according to claim 1 wherein said actuator has a cylindrical or fiber-shaped configuration extending in the expanding and contracting direction of said intercalation substance, and is coated with an elastic porous organic polymer that defines fine holes permitting the solution to pass through, at least a part of the side surface of said actuator.

7. The driving system according to claim 1 wherein said actuator is made up of a plurality of serially connected elements each having a cylindrical or fiber-shaped configuration extending in the expanding or contracting direction of said intercalation substance.

8. The driving system according to claim 1 wherein said actuator has a structure in which a plurality of serially connected elements each having a cylindrical or fiber-shaped configuration extending in the expanding and contracting direction of said intercalation substance form a unit, and a plurality of said units are connected in parallel.

9. The driving system according to claim 1 wherein said actuator has a film-shaped or plate-shaped configuration having a major surface extending vertically of the expanding and contracting direction of said intercalation substance.

10. The driving system according to claim 1 wherein said actuator has a film-shaped or plate-shaped configuration having a major surface extending vertically of the expanding and contracting direction of said intercalation substance, and is coated with an elastic, porous organic polymer that defines fine holes permitting the solution to pass through, at least in a part of the surface of said actuator.

11. The driving system according to claim 1 wherein said actuator is made up of a plurality of serially connected elements each having a film-shaped or plate-shaped configuration having a major surface that extends vertically of the expanding and contracting direction of said intercalation substance.

12. The driving system according to claim 1 wherein said actuator has a structure in which a plurality of serially connected elements each having a film-shaped or plate-shaped configuration having a major surface extending in the expanding and contracting direction of said intercalation substance form a unit, and a plurality of said units are connected in parallel.

13. The driving system according to claim 1 wherein said actuator is an element shaped from said intercalation substance in powder.

14. The driving system according to claim 1 wherein said actuator is a member shaped from said intercalation substance in powder, ad coated with an elastic, porous organic polymer that defines fine holes permitting the solution to pass through, at least in a portion of the surface of said actuator.

15. The driving system according to claim 1 wherein said actuator is made up of a plurality of serially connected elements each shaped from said intercalation substance in powder.

16. The driving system according to claim 1 wherein said actuator has a structure in which a plurality of serially connected elements each shaped from said intercalation substance in powder form a unit, and a plurality of said units are connected in parallel.

17. The driving system according to claim 1 wherein said actuator is made up of a tubular hollow element made of an elastic material defining fine holes permitting the solution to pass through, and said intercalation substance bonded around said hollow element such that the expanding and contracting direction of said intercalation substance is parallel with the axial direction of said hollow element.

18. The driving system according to claim 1 wherein the solution is supplied inside said hollow element from said solution supply means.

19. The driving system according to claim 1 wherein said hollow element is a hollow yarn.

20. The driving system according to claim 1 wherein said actuator has a bimorph structure in which a first actuator using a first intercalation substance and a second actuator using a second intercalation substance are bonded vertically of the expanding and contracting direction of said first intercalation substance and said second intercalation substance.

21. The driving system according to claim 1 wherein said actuator has a unimorph structure in which said intercalation substance and an elastic member are bonded vertically of the expanding and contracting direction of said intercalation substance.

22. The driving system according to claim 1 wherein said solution supply means is configured to supply the solution to actuator while collecting the solution to use it again.

23. The driving system according to claim 1 wherein said solution supply means is configured to supply the solution to said actuator while discarding at least a part of said solution and replacing the discarded part with fresh solution.

24. The driving system according to claim 1 wherein said actuator is contained in a container, and said solution supply means includes at least one solution supply tube connected to one and the other ends of said container to form a closed flow circuit passing through said container.

25. The driving system according to claim 24 including a plurality of said solution supply tubes.

26. The driving system according to claim 24 including, enroute of said solution supply tube, a pump for sending out the solution to said container and a drainage treatment portion for refining the solution discharged from said actuator.

27. The driving system according to claim 26 wherein said drainage treatment portion refines the solution by ion exchange.

28. The driving system according to claim 1 wherein said solution supply tube includes a first solution supply tube that supplies a first solution for expanding said intercalation substance, and a second solution supply tube that supplies a second solution for contracting said intercalation substance.

29. The driving system according to claim 28 wherein said first solution supply tube and said second solution supply tube are connected to one and the other ends of said actuator via control valves that are controlled in opening and closing state in response to expansion and contraction of said actuator.

30. The driving system according to claim 1 wherein said actuator is made up of a first actuator and a second actuator that share a common support, and antagonistically expand and contract.

31. The driving system according to claim 1 wherein said actuator form an artificial muscle.

32. The driving system according to claim 1 wherein a host substance of said intercalation substance contains at least one kind of inorganic layered substances, and a guest substance of said intercalation substance is ions or molecules, such that ingress and egress of said guest substance to and from a space between layers of said host substance cause an intercalation reaction and thereby cause changes in distance between layers to drive said actuator.

33. The driving system according to claim 32 wherein said host substance is an inorganic/organic composite substance made by intercalating at least one kind of inorganic substances to a space between layers of an inorganic layered substance, and said actuator is driven by changing the distance between layers by ingress and egress of the guest substance relative to said host substance.

34. The driving system according to claim 32 wherein said host substance is immersed in a solution containing said guest substance, and said solution containing the guest substance is replaced with a solution not containing the guest substance, such that said guest substance is reversibly entered into and removed from a space between layers of said host substance to cause changes in distance between layers and thereby drive said actuator.

35. The driving system according to claim 32 wherein said host substance is immersed in a solution containing said guest substance, and said solution containing the guest substance is changed in concentration, such that said guest substance is reversibly entered into and removed from a space between layers of said host substance to cause changes in distance between layers and thereby drive said actuator.

36. The driving system according to claim 32 wherein said guest substance is an organic substance.

37. The driving system according to claim 32 wherein at least one polar functional group exists at least in one of carbon positions of said organic substance.

38. The driving system according to claim 32 wherein said inorganic layered substance of said host substance is at least one kind of substance selected from the group consisting of layered perovskite, niobium-series substances, layered perovskite copper-series substances, layered titanium niobates, layered halite oxides, transition metal oxides bronze-series substances, transition metal oxochlorides, layered polysilicates, layered clay minerals, hydrotalcites, transition metal chalcogenides, phosphoric acid zirconates and graphite.

39. The driving system according to claim 32 wherein an acidic solution and/or a alkali metal hydroxide solution is used to disconnect said guest substance from said host substance.

40. The driving system according to claim 32 wherein said guest substance is amine, and hydrochloric acid is used to disconnect said guest substance from said host substance.

41. An actuator using an intercalation substance and driven by exchange of solutions or by changing concentration of a solution.

42. An actuator comprising:
   a plurality of layered host compounds in contract with a liquid; and
   a guest compound intercalated between layers of a plurality of layered host compounds,
   said actuator being driven by replacing said guest compound with another guest compound by change of the state of surrounding liquid.

43. The actuator according to claim 42 wherein said change of the state is a change of kinds of solutions.

* * * * *